United States Patent
Rosenberg et al.

[11] Patent Number: 6,070,467
[45] Date of Patent: *Jun. 6, 2000

[54] ELECTROMAGNETIC ACOUSTIC TRANSDUCER (EMAT) SYSTEM AND METHOD FOR ELIMINATING NOISE PRODUCED BY STATIC DISCHARGE

[75] Inventors: Jeffrey S. Rosenberg, Broken Arrow; Mark Land, Owasso; Pat Cook, Skiatook, all of Okla.

[73] Assignee: Gas Research Institute, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/953,081

[22] Filed: Oct. 17, 1997

[51] Int. Cl.⁷ .............................. G01N 9/24; G01N 29/00; H04R 23/00
[52] U.S. Cl. ................................ 73/643; 73/644; 367/140
[58] Field of Search ...................... 73/643, 644; 324/226, 324/227; 367/140

[56] References Cited

U.S. PATENT DOCUMENTS

| | | | |
|---|---|---|---|
| 4,149,421 | 4/1979 | Bottcher et al. | 73/643 |
| 4,296,486 | 10/1981 | Vasile | 73/643 |
| 5,050,703 | 9/1991 | Graff et al. | 181/106 |
| 5,140,860 | 8/1992 | Hüschelrath et al. | 73/643 |
| 5,164,921 | 11/1992 | Graff et al. | 367/140 |
| 5,299,458 | 4/1994 | Clark, Jr. et al. | 73/597 |
| 5,436,873 | 7/1995 | MacLauchlan et al. | 367/140 |
| 5,526,691 | 6/1996 | Latimer et al. | 73/592 |
| 5,537,876 | 7/1996 | Davidson et al. | 73/624 |
| 5,608,691 | 3/1997 | MacLuachlan et al. | 367/140 |
| 5,684,406 | 11/1997 | MacLauchlan et al. | 324/700 |

*Primary Examiner*—Helen C. Kwok
*Attorney, Agent, or Firm*—Pauley Petersen Kinne & Fejer

[57] ABSTRACT

The present invention allows for the fabrication of an EMAT system that eliminates static charge impulse noise. The EMAT system includes an EMAT, wear layer, and magnet. If the wear layer is made slightly conductive, the static charges slowly bleed off rather than build up to cause impulse discharges. This semiconductive wear layer does not attenuate the EMAT signals by introducing any additional distance between the EMAT coil and the conductive piping or by introducing any conductive material between the EMAT coil and the conductive piping. In the preferred embodiment, a wear layer of UHMW (ultra high molecular weight) polyethylene with a surface resistivity of about 10,000 ohms per square is utilized. The conductive UHMW polyethylene still acts as a wear layer, but now also acts as a semi-conductive static-dissipative interface between the EMAT coil and the piping.

14 Claims, 1 Drawing Sheet

ELECTROMAGNETIC ACOUSTIC TRANSDUCER (EMAT) SYSTEM AND METHOD FOR ELIMINATING NOISE PRODUCED BY STATIC DISCHARGE

FIELD OF THE INVENTION

The present invention generally relates to ultrasonic testing using electromagnetic acoustic transducers (EMATs) and, more particularly, to an improved EMAT system and method for inspecting conductive piping in a manner that substantially eliminates noise produced by microscopic static discharges within the system.

BACKGROUND

The need for non-destructive detection of defects in piping is necessary to avoid costly shut down of equipment and for ensuring the integrity of aged piping, specifically where the aged piping is carrying high pressure combustible fluids and gases that pose a significant safety or health hazard. Potential defects affecting the quality and effectiveness of piping may include, but are not limited to flaws such as cracks, dents, and pits.

Traditionally, the non-destructive testing of piping was accomplished through systems utilizing ultrasonic piezoelectric transducers that were coupled to the surface by a fluid or gel. However, the use of a couplant creates numerous problems reducing the overall effectiveness of the system, and it is, therefore, desirable to develop and use other types of inspection systems.

As an alternative to piezoelectric transducers, techniques utilizing ultrasonic inspection of conductive surfaces have been developed. These techniques use electromagnetic acoustic transducers (EMATs) to transmit, without the use of a couplant, an ultrasonic wave into the piping.

In order to generate the ultrasonic wave, the EMAT induces eddy currents at the surface of the conductive piping under test. These induced eddy currents interact with the magnetic field produced by an electromagnet or permanent magnet located near the EMAT. The result of the interaction is a Lorentz force that acts upon the conductive piping to produce an ultrasonic wave.

Until a defect is encountered, the induced ultrasonic wave propagates through the conductive piping. The interaction between the defect encountered and the ultrasonic wave causes the propagated wave to reflect back toward the EMAT. Once the reflected ultrasonic wave reaches the EMAT, the EMAT's receiver is responsible for receiving and processing the low level reflected signals. As such, this instrumentation is susceptible to noise pick up from many sources.

In order to eliminate specific sources of noise, shielding of the EMAT is usually performed. As an example, MacLauchlan (U.S. Pat. No. 5,608,691), which is incorporated herein by reference, discloses a shield for an EMAT that has multiple alternating layers of electrically insulating and electrically conductive materials which encapsulate the EMAT in order to substantially shield the EMAT from electrostatic noise. A primary source of electrostatic noise is AM radio signals. Although other simple shields (such as a pieces of aluminum foil) attenuate both the AM radio signals and the EMAT signals, the MacLauchlan shield is capable of attenuating most of the electrostatic (AM radio) noise, while keeping the EMAT signal attenuation to a minimum.

Although the MacLauchlan shield effectively attenuates electrostatic noise, there are still other forms of noise that affect the performance of an EMAT and are not attenuated by current shielding techniques. Thus, a heretofore unaddressed need exists in the industry of reducing the unattenuated noise in current EMAT design.

SUMMARY OF INVENTION

The present invention is an electromagnetic acoustic transducer (EMAT) system and method that dissipates static charges within a wear layer. The EMAT system is composed of an EMAT, wear layer, and magnet. In order to dissipate static charges, the wear layer is made of a semi-conductive material. The magnet provides an electromagnetic field used in inducing a ultrasonic wave.

An advantage of the EMAT system and method of the present invention is that they provide for an improved EMAT system that eliminates static charge impulse noise.

By making the wear layer semiconductive, the static charges slowly bleed off rather than build up to cause impulse discharges. This semiconductive layer eliminates static charge impulse noise without any significant attenuation of the EMAT signals.

Other features and advantages of the present invention will become apparent to one skilled in the art upon examination of the following description, drawings, and claims.

BRIEF DESCRIPTION OF THE DRAWINGS

The present invention can be better understood with reference to the following drawing. The drawing is not necessarily to scale, emphasis is instead being placed upon clearly illustrating the principles of the present invention.

DETAILED DESCRIPTION OF THE INVENTION

Figure 1:
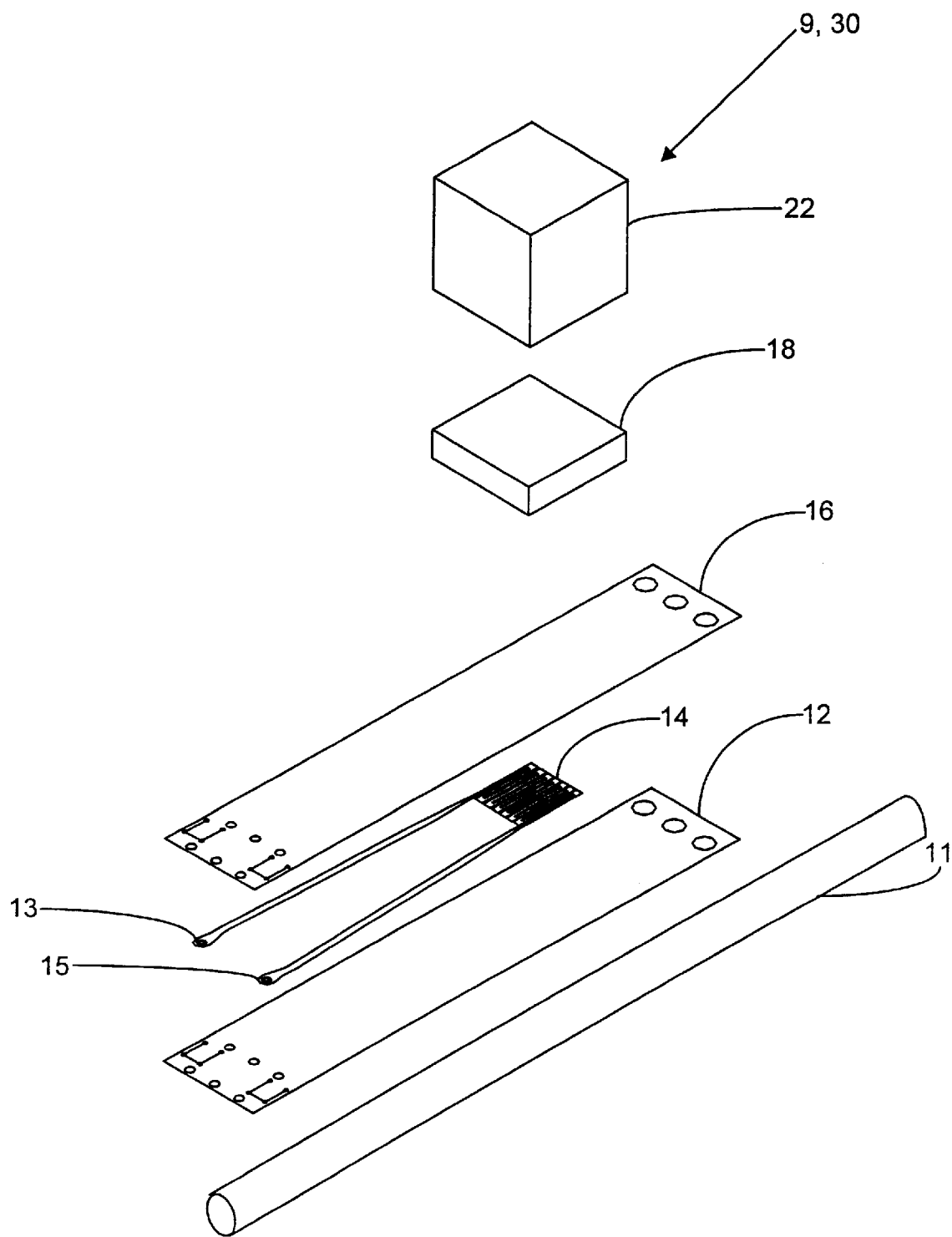
FIG. 1 is an exploded-perspective view of an EMAT constructed in accordance with the prior art and the present invention.

FIG. 1 depicts a typical electromagnetic acoustic transducer (EMAT) system 9 used to detect defects in a conductive pipe 11. Referring to FIG. 1, the wear layer 12 is an inner protective layer positioned between an EMAT 14 and the conductive pipe 11. Typically, the wear layer 12 is fabricated from ultra high molecular weight (UHMW) polyethene and is about 0.01 inches thick. The wear layer 12 protects the EMAT 14 as the system 9 is moved across the surface of the pipe 11. The EMAT 14 is typically etched from a sheet of copper in such a way that EMAT 14 includes coils, and the wear layer 12 is typically fabricated from insulating material to prevent EMAT 14 from shorting with the conductive pipe 11.

The EMAT 14 is typically positioned between the wear layer 12 and a thin outer protective layer 16. A sponge 18 usually separates a magnet 22 from outer protective layer 16. The sponge prevents debris from collecting underneath magnet 22 and is preferably fabricated from a soft material. Magnet 22 creates a magnetic field that extends through the EMAT 14 and into the conductive piping 11. It is well known in the art that the magnet 22 can be configured as a permanent magnet or an electromagnet. Pulsing the EMAT 14 with an oscillating current generates an ultrasonic signal that propagates through the pipe 11. A typical peak to peak current level pulsed in the EMAT 14 is about 120 amps.

When the propagated wave encounters a defect in pipe 11, part of the wave is reflected back to system 9. As known in the art, the system 9 detects defects in pipe 11 by receiving and processing this reflected signal.

In order to receive the reflected ultrasonic signals, a high gain amplifier (not shown) and processing elements (not shown) are attached across the terminals 13 and 15 of the EMAT 14 according to techniques well-known in the art. Typically, an amplifier gain of about 120 dB (1,000,000:1) is utilized. Furthermore, the transmit-to-receive insertion loss is very high with EMAT 14. The typical amplitudes of ultrasonic signals received at the EMAT 14 are fractions of a microvolt. With high gain amplifiers and tiny signal levels, noise limits the performance of the system 9. Eliminating any source of noise improves the performance of the EMAT system 9.

While working to reduce noise within system 9, a new impulse noise source was discovered. The impulse noise closely resembles the reflected signals making filtering difficult if not impossible. A considerable array of tests were performed to isolate the source of this newly discovered impulse noise. From these tests, it has been determined that the noise is caused by the rubbing of the wear layer 12, against the conductive pipe 11. This rubbing action generates static charges which build up and then rapidly discharge when the EMAT 14 is moved across the conductive piping. The discharge generates electromagnetic interference (EMI) that couples into the high gain EMAT receiver amplifier (not shown). As a result, any reflected ultrasonic waves are masked by the noise induced from static discharges during the discharge interval.

Upon discovering the aforementioned new source of noise, the system 30 of the present invention was designed. Referring to FIG. 1, the system 30 of the present invention differs from system 9 of the prior art in that wear layer 12 is configured to be semi-conductive. As used herein, a semi-conductive material is any conductive material with a resistivity or conductivity in the range between metals and insulators. By fabricating the wear layer 12 with a static dissipative material, the static charges within the wear layer 12 slowly dissipate into the conductive piping 11 instead of building up to cause impulse discharges.

In the preferred embodiment, the wear layer 12 is constructed of UHMW polyethene with a surface resistivity of about 10,000 ohms per square. However, any semiconductive material is sufficient so long as the static charges within wear layer 12 are allowed to dissipate. For example, if the static charges created within wear layer 12 are not sufficiently dissipating to prevent significant impulse noise, then the material of wear layer 12 should be changed to a material having a lower resistivity in order to make wear layer 12 more conductive for the given conditions. However, if the reflected signal received by EMAT 14 is significantly attenuated, then the material of wear layer 12 should be changed to a material having a higher resistivity in order to make wear layer 12 less conductive for the given conditions. By using the foregoing procedures, a semiconductive material can be found where the static charges of wear layer 12 are sufficiently dissipated to prevent rapid discharges and where the reflected ultrasonic signal is not significantly attenuated. As a result, the impulse noise caused by rapid static discharges from wear layer 12 can be effectively eliminated while preserving the reflected ultrasonic signal.

It should be noted that materials with a surface resistivity ranging from about $10^5$ ohms to $10^8$ ohms are typically considered to be static dissipative. Therefore, materials having a surface resistivity within the foregoing range should sufficiently dissipate electric charges within wear layer 12 as described hereinabove. However, materials outside of the foregoing resistivity range may also sufficiently dissipate the electric charges within wear layer 12 according to the principles discussed hereinbefore, and the present invention should not be limited to only materials having a surface reisistivity within the foregoing resistivity range.

In addition to providing an apparatus for dissipating static charges, the present invention also provides a method, as described above, for fabricating the EMAT system 30.

In concluding the detailed description, it should be noted that it will be apparent to those skilled in the art that numerous variations and modifications may be made to the preferred embodiment without departing from the principles of the present invention. All such variations and modifications are intended to be included herein within the scope of the present invention, as set forth in the claims.

What is claimed is:

1. An electromagnetic acoustic transducer (EMAT) system for non-destructive testing of piping, comprising:
    an EMAT;
    a static dissipative wear layer having a surface resistivity between about $10^5$ ohms to $10^8$ ohms coupled directly to said EMAT and configured to dissipate static charges within said wear layer to prevent static discharge from occurring between said piping and said EMAT; and
    a magnet positioned such that a magnetic field produced by said magnet passes through said EMAT.

2. The EMAT of claim 1, wherein said EMAT is etched from a sheet of copper.

3. The EMAT of claim 1, wherein said wear layer is made of a flexible abrasion resistant material.

4. The EMAT of claim 1, wherein said magnet is a permanent magnet.

5. The EMAT of claim 1, wherein said magnet is a electromagnet.

6. The EMAT of claim 1, wherein said wear layer eliminates impulse static discharge noise.

7. The EMAT of claim 1, wherein said EMAT generates an ultrasonic wave and receives a reflection of said wave.

8. The wear layer of claim 3, wherein said wear layer is made of a slightly conductive material.

9. The wear layer of claim 3, wherein said wear layer is made of UHMW polyethylene.

10. The UHMW polyethylene of claim 9, wherein said UHMW polyethylene is made with an electrical resistance that makes it static dissipating.

11. A method for fabricating an electromagnetic acoustic transducer (EMAT) system that dissipates static charges, comprising the steps of:
    fabricating a wear layer with resistive characteristics to make said wear layer static dissipating, wherein said wear layer is fabricated with static dissipative material having a surface resistivity between about $10^5$ ohms to $10^8$ ohms;
    fabricating an EMAT; and
    coupling said wear layer directly to said EMAT to prevent static discharge from occurring between said piping and said EMAT.

12. A method of detecting defects within piping, comprising the steps of:
    fabricating a static dissipative wear layer having a surface resistivity between about $10^5$ ohms to $10^8$ ohms;
    coupling said wear layer directly to an EMAT;
    propogating an ultrasonic wave through said piping;
    receiving and processing a reflection of said wave; and
    slowly dissipating static charges within said static dissipative wear layer, into said piping to prevent static discharge from occurring between said piping and said EMAT.

13. An electromagnetic acoustic transducer (EMAT) system for non-destructive testing of piping, comprising:
    an EMAT;
    a static dissipative wear layer having a surface resistivity between about $10^5$ ohms to $10^8$ ohms coupled with respect to said EMAT to form a single layer between said piping and said EMAT and configured to dissipate static charges within said wear layer to prevent static discharge from occurring between said piping and said EMAT; and a magnet positioned such that a magnetic field produced by said magnet passes through said EMAT.

14. A method for fabricating an electromagnetic acoustic transducer (EMAT) system that dissipates static charges during the non-destructive testing of piping, comprising the steps of:

fabricating a wear layer with resistive characteristics to make said wear layer static dissipating, wherein said wear layer is fabricated with a single static dissipative material having a surface resistivity between about $10^5$ ohms to $10^8$ ohms;

fabricating an EMAT; and coupling said wear layer with respect to said EMAT to form a single layer to prevent static discharge from occurring between said piping and said EMAT.

* * * * *

UNITED STATES PATENT AND TRADEMARK OFFICE
CERTIFICATE OF CORRECTION

PATENT NO : 6,070,467
DATED : 06 June 2000
INVENTOR(S) : Jeffrey S. ROSENBERG et al.

It is certified that error appears in the above-identified patent and that said Letters Patent are hereby corrected as shown below:

In Column 4, line 42, after "charges" insert -- during the non-destructive testing of piping --

Signed and Sealed this

Twenty-second Day of May, 2001

*Attest:*

NICHOLAS P. GODICI

*Attesting Officer*   *Acting Director of the United States Patent and Trademark Office*